(12) United States Patent
Salvador et al.

(10) Patent No.: US 10,450,537 B2
(45) Date of Patent: Oct. 22, 2019

(54) SOLID CONCENTRATE COMPOSITIONS CONTAINING ZINC PYRITHIONE

(71) Applicant: The Procter & Gamble Company, Cincinnati, OH (US)

(72) Inventors: Charlie Reyes Salvador, Singapore (SG); Chunpeng Jiang, Beijing (CN); Yanan Sun, Beijing (CN); Zhe Liu, Beijing (CN); Gbenga Segun Showole, Lagos (NG); Anurag Makrandi, Singapore (SG); Raul Songco Nicdao, Paranaque (PH)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/853,558

(22) Filed: Sep. 14, 2015

(65) Prior Publication Data

US 2017/0191009 A1 Jul. 6, 2017
US 2019/0276780 A9 Sep. 12, 2019

Related U.S. Application Data

(63) Continuation of application No. 14/853,489, filed on Sep. 14, 2015.

(30) Foreign Application Priority Data

Mar. 14, 2013 (WO) ................ PCT/CN2013/072648
Apr. 18, 2013 (WO) ................ PCT/CN2013/074366
(Continued)

(51) Int. Cl.
C11D 9/34 (2006.01)
C11D 13/14 (2006.01)
(Continued)

(52) U.S. Cl.
CPC ............... *C11D 9/34* (2013.01); *C11D 3/48* (2013.01); *C11D 9/10* (2013.01); *C11D 9/20* (2013.01); *C11D 9/32* (2013.01); *C11D 13/14* (2013.01)

(58) Field of Classification Search
None
See application file for complete search history.

(56) References Cited

U.S. PATENT DOCUMENTS 3,269,904 A * 8/1966 Bernstein ............. C07D 213/89
514/345
4,161,526 A 7/1979 Gorman
(Continued)

FOREIGN PATENT DOCUMENTS

EP 2968079 B1 8/2017
JP 2001278863 A 10/2001
(Continued)

OTHER PUBLICATIONS

Felhosi et al., Effects of Bivalent Cations on Corrosion Inhibition of Steel by 1-Hydroxyethane-1,1-diphosphonic Acid, Journal of the Electrochemical Society, 146(3), pp. 961-969 (1999).
(Continued)

*Primary Examiner* — Necholus Ogden, Jr.

(57) ABSTRACT

The present invention relates to a solid concentrate composition comprising: (a) from 5% to 25% by weight of zinc pyrithione (ZPT); (b) from 8% to 85% by weight of at least one surfactant, preferably, wherein the solid concentrate composition has a penetration hardness of between 20 N and 50 N according to the test method as disclosed herein.

6 Claims, 3 Drawing Sheets

(30) Foreign Application Priority Data

Feb. 26, 2014 (WO) ................ PCT/CN2014/072565
Feb. 28, 2014 (WO) ................ PCT/CN2014/072729

(51) Int. Cl.
*C11D 9/32* (2006.01)
*C11D 9/10* (2006.01)
*C11D 9/20* (2006.01)
*C11D 3/48* (2006.01)

(56) References Cited

U.S. PATENT DOCUMENTS

| | | | |
|---|---|---|---|
| 4,482,715 A | 11/1984 | Trotz et al. | |
| 4,533,736 A | 8/1985 | Trotz et al. | |
| 4,818,436 A | 4/1989 | French et al. | |
| 4,957,658 A | 9/1990 | French et al. | |
| 5,883,154 A | 3/1999 | Kappock et al. | |
| 5,929,012 A | 7/1999 | Del Duca et al. | |
| 6,110,883 A | 8/2000 | Petri et al. | |
| 8,673,274 B2 | 3/2014 | Schwartz et al. | |
| 9,668,474 B2 | 6/2017 | Hawkins et al. | |
| 9,877,905 B2 | 1/2018 | Dixon et al. | |
| 2003/0211955 A1* | 11/2003 | Puvvada | C11D 3/046 510/141 |
| 2004/0253194 A1 | 12/2004 | Rioux et al. | |
| 2005/0123503 A1 | 6/2005 | Kozasa et al. | |
| 2006/0111259 A1* | 5/2006 | Chakrabarty | A61K 8/26 510/141 |
| 2008/0206355 A1 | 8/2008 | Schwartz et al. | |
| 2013/0045263 A1 | 2/2013 | Smith, III et al. | |
| 2013/0045961 A1 | 2/2013 | Smith, III et al. | |
| 2016/0074300 A1 | 3/2016 | Salvador et al. | |

FOREIGN PATENT DOCUMENTS

| | | |
|---|---|---|
| WO | WO0100151 A1 | 1/2001 |
| WO | WO03088957 A1 | 10/2003 |
| WO | WO2006053708 A1 | 5/2006 |
| WO | WO2013166718 A1 | 11/2013 |

OTHER PUBLICATIONS

International Preliminary Report on Patentability and Written Opinion of the International Searching Authority, PCT/CN2014/073389, dated Sep. 24, 2015, 8 pages.
Polson et al., Iron Deprivation as a Strategy to Potentiate Topical Antimicrobials, International Federation of Societies of Cosmetic Chemists (IFSCC), Poster # 75, 2012.
Supplementary International Search Report, PCT/CN2014/073389, dated Jun. 29, 2015, 7 pages.
All Office Actions, U.S. Appl. No. 14/208,821, filed Mar. 13, 2014.
All Office Actions, U.S. Appl. No. 14/853,629, filed Sep. 14, 2015.
All Office Actions, U.S. Appl. No. 14/255,714, filed Apr. 17, 2014.

* cited by examiner

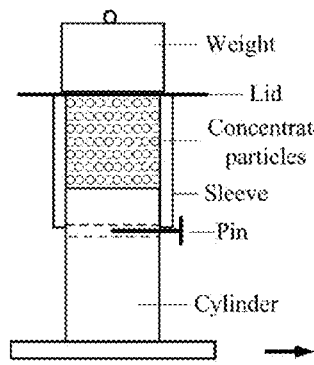
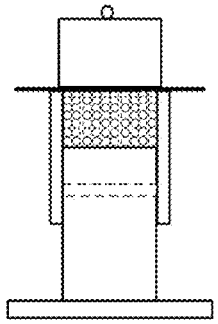
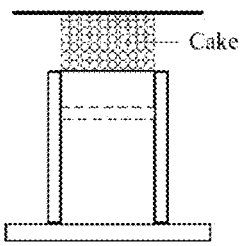
FIG. 2A   FIG. 2B   FIG. 2C
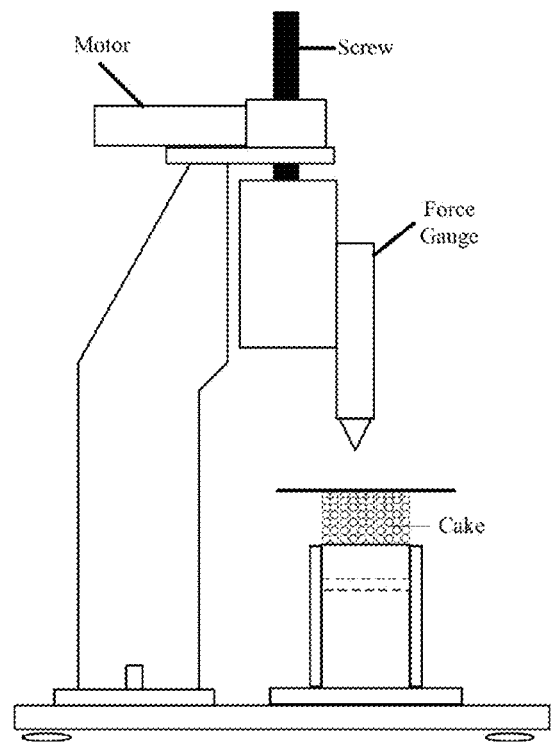
FIG. 2D

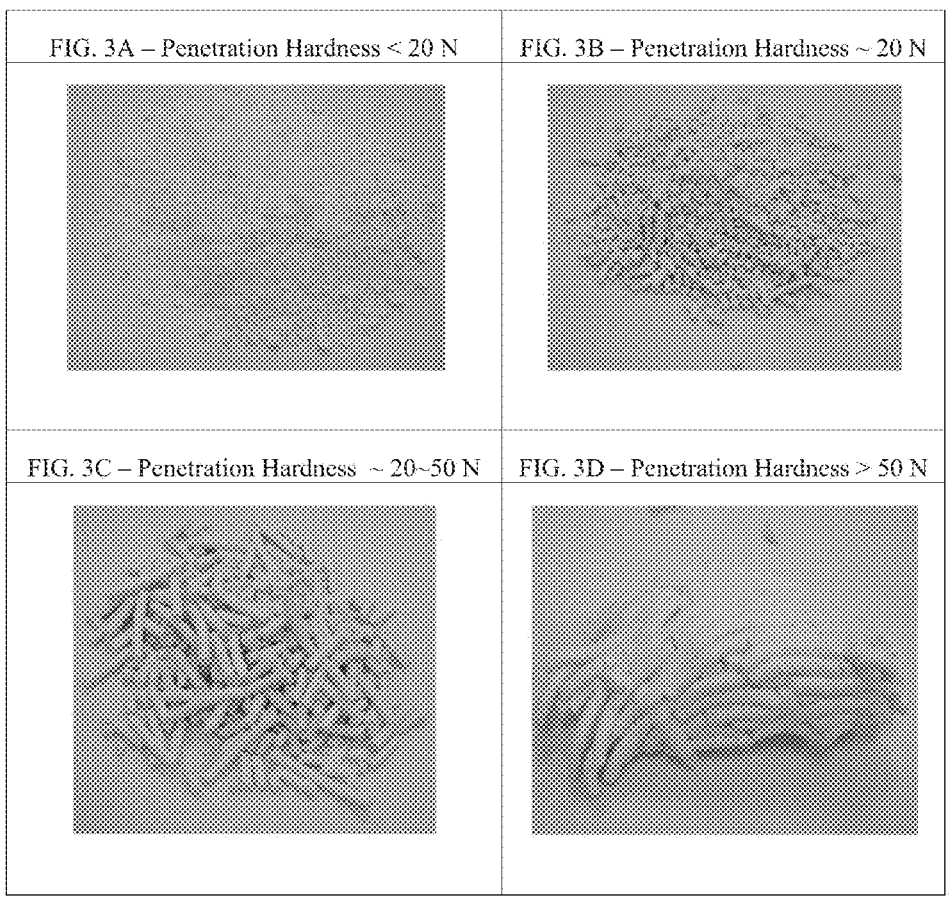

SOLID CONCENTRATE COMPOSITIONS CONTAINING ZINC PYRITHIONE

FIELD OF THE INVENTION

The present invention relates to solid concentrate compositions comprising zinc pyrithione (ZPT).

BACKGROUND OF THE INVENTION

Pyrithione (also known as 1-Hydroxy-2-pyridinethione, 2-pyridinethiol-1-oxide, 2-mercaptopyridine-N-oxide, pyridine-2-thione-N-oxide, pyridinethione-N-oxide, 2-pyridinethione, pyridinethione, or simply "PT") has been noted for its bactericidal and fungicidal activities. Pyrithione is a bidentate ligand that forms stable complexes with most transitional metals. Metallization of pyrithione often results in highly augmented biocidial activities. Metal salts of pyrithione, such as for example, sodium pyrithione, magnesium pyrithione, barium pyrithione, bismuth pyrithione, strontium pyrithione, copper pyrithione, zinc pyrithione, cadmium pyrithione, and zirconium pyrithione, are widely used as fungicides and bactericides in a broad spectrum of commercial products, such as metalworking fluids, lubricants, paints, cosmetics and toiletries.

Zinc pyrithione (or "ZPT") is especially useful as a broad-spectrum anti-microbial agent and preservative. It is active against both gram-positive and gram-negative bacteria, as well as fungi and yeasts. Therefore, ZPT has been used in various personal care compositions, such as for example, anti-dandruff shampoos, hair conditioners, leave-on tonics, and anti-microbial foot powders. Bar soap is a popular product form for cleansing. A bar soap comprising ZPT is particularly desirable for its broad-spectrum anti-microbial efficacy.

ZPT is a crystalline solid that can generally be mixed into a soap composition from either a powder form, or from a liquid dispersion. Powder form can be difficult to handle because they can generate dust during dosing and mixing. As a result, powder form may require complex and expensive dust handling equipment. Although liquid dispersions are generally easier to handle, they can have their own complexities for shipping, storing and processing. For example, liquid slurries must be regularly stirred during processing to avoid settling, and accurately dosed in every manufacturing line. Additionally, liquid slurries are usually maintained in a system requiring extensive cleaning, sanitizing and wastewater recovery, and may even require a separate preservative just for the liquid slurry. Therefore, a need exist for a convenient means to dose ZPT into a soap composition that can overcome these difficulties.

SUMMARY OF THE INVENTION

The present invention is directed to a solid concentrate composition comprising: (a) from 5% to 25% by weight of a zinc pyrithione (ZPT), and (b) from 8% to 85% by weight of at least one surfactant. In an embodiment, the solid concentrate composition has a penetration hardness of between 20 N and 50 N. These and other aspects of the present invention will become more apparent upon reading the following drawings and detailed description of the invention.

BRIEF DESCRIPTION OF THE DRAWINGS

FIGS. 2A-2C depict the cylinder, sleeve and weight used to form the cake form from the concentrate compositions for the penetration hardness test.

FIG. 2D shows the Force Gauge Machine (Model 2-44; IMADA Inc., Ill., USA) used for the penetration hardness test.

FIGS. 3A-D are photos of solid concentrate compositions of varying penetration hardness.

DETAILED DESCRIPTION OF THE INVENTION

Figure 1:
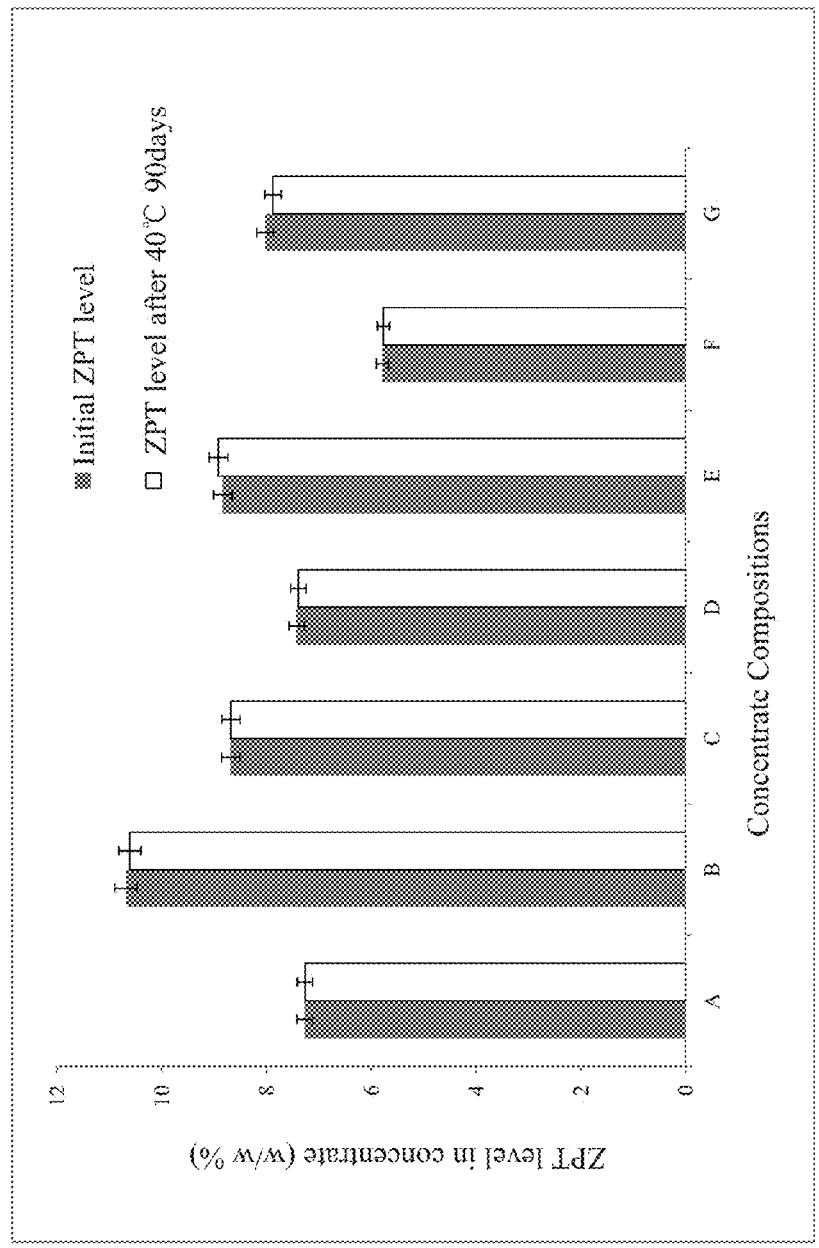
FIG. 1 is a bar graph showing the percentage loss of ZPT in seven (7) ZPT-containing concentrate compositions of the present invention.

Except as otherwise noted, the articles "a", "an", and "the" mean "one or more."

The term "comprising" means that other steps and other ingredients which do not affect the end result can be added, and this term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein. Particularly, the compositions of the present invention contain ZPT, and one or more additional or optional ingredients as described hereinafter.

All percentages, parts and ratios are based upon the total weight of the compositions of the present invention, unless otherwise specified. All such weights as they pertain to listed ingredients are based on the active level and, therefore do not include carriers or by-products that may be included in commercially available materials. The components, including those which may optionally be added, as well as methods for preparation, and methods for use, are described in detail below.

"Solid" as used herein refers to concentrate compositions that are solid (i.e., dry and not flowable like a liquid or semi-liquid) at about 15% relative humidity, and at about 25° C., unless otherwise specified. The concentrate composition in solid form can be in the form of an agglomerate, granule, flake, extrudate, bar, tablet or any combination thereof. Preferably, the term "solid" refers to materials that have a penetration hardness of 20 N to 50 N as measured by a Force Gauge Machine (Model Z2-44) available from IMADA Inc. (Illinois, USA) according to the test method as described herein.

"Penetration hardness" as used herein is a reflection of how much force (N) is required to break a cake formed from the concentrate composition of the present invention according to the test method as described herein. "Penetration hardness" is also a way to represent the stickiness of the concentrate composition. For example, higher values represent more sticky material, and lower values represent more powdery material.

"Bar soaps" as used herein refers to solid or semi-solid articles for washing, bathing, and cleaning that contain either soap surfactants, synthetic surfactants, or mixtures thereof (i.e., semi-synthetics) as described hereinafter. A bar soap as used herein is not limited to a bar shape but can have any regular or irregular shape, including but not limited to: cubic, rectangular, spherical, oval, cylindrical, pyramidal and the like. The bar soaps of the present invention are preferably, but not necessarily, characterized by a volume ranging from 1 cm$^3$ to 1,000 cm$^3$, more preferably from 10 cm$^3$ to 500 cm$^3$, and most preferably from 50 cm$^3$ to 200 cm$^3$, and a weight ranging from 0.5 g to 5 Kg, more preferably from 1 g to 1 Kg, and most preferably from 10 g to 500 g.

Solid Concentrate Compositions

The present invention relates to a solid concentrate composition comprising: (a) from 5% to 25% by weight of a zinc pyrithione (ZPT); and (b) from 8% to 85% by weight of at least one surfactant.

The inventors have found a simple and reliable means to dose ZPT into a soap composition by concentrating the ZPT active into a solid concentrate composition having from 5% to 25% by weight of a ZPT. For example, a solid concentrate composition can be prepared at a concentration about 10-fold or even greater, higher than the desired ZPT concentration in the soap composition. Such a ZPT-containing solid concentrate composition can be prepared at one single manufacturing station and cost effectively shipped in its compacted form to other sites for dilution with standard medium known to those skilled in the art to form finished products.

The solid concentrate composition thus prepared is easy to store, transport, and add to any soap manufacturing line using simple equipment that already exists on soap manufacturing lines, without the need for incurring additional complex material handling capital. Because the concentrate composition is a solid with compliant properties, like a soap noodle, it is easy to distribute the concentrate composition throughout the whole soap batch homogeneously during the soap manufacturing process by the conventional soap milling and extruding operations. For example, the solid concentrate composition can be diluted into solid bar soaps. Alternatively, the solid concentrate composition can be dissolved into a liquid tank to form liquid soap compositions.

According to one embodiment, the concentrate composition further comprises (c) from 1.4% to 15% by weight of a chelant, wherein the chelant has a log $K_{ZnL}$ of greater than 2, wherein the log $K_{ZnL}$ is the log of a conditional stability constant of the chelant with Zn calculated at pH 7, 25° C., 0.1 M NaCl. Preferably, the chelant has a Conditional Stability Constant for zinc higher than 3, and more preferably higher than 6. It has been found that in order to maintain a desired level of the affinity for the chelant, the pH of the concentrate composition further comprises a sufficient quantity of a buffer system comprising an organic acid and/or a salt thereof to provide the concentrate composition with a pH from about 4 to about 11 at 25° C. The conditional stability constant is a parameter commonly used in the art to practically assess the stability of metal-chelant complex at a given pH. A detailed discussion on conditional stability constant can be found for example in "Dow Chelating Agents" published by Dow Chemical Company Limited, and U.S. Publication US2013/0174863 (P&G), incorporated herein by reference. The calculated stability constants for a range of chelants with Zn are given below in Table 1:

TABLE 1

Calculated Conditional Stability Constants for Chelants with Zn at specified pH (log Conditional Stability Constant*)

| Chelants | Zn (pH 7) | Zn (pH 10) |
| --- | --- | --- |
| HPNO | 5.1 | 5.1 |
| HEDP | 7.3 | 10.1 |
| EDTA | 14.0 | 16.4 |

*Ionic strength of 0.1.

In another embodiment, the concentrate composition further comprises (c) from 1.4% to 15% be weight of a chelant, wherein the chelant is a metal phosphonate complex comprising one or more phosphonate chelants co-ordinately bonded to one or more metal ions. In yet another embodiment, the concentrate composition further comprises (c) from 1.4% to 15% by weight of a chelant, wherein the chelant is a metal-pyridine oxide complex that is co-ordinately bonded to a metal ion. Alternatively, the concentrate composition of the present invention further comprises (c) from 1.5% to 5%, or 3% to 10%, or 10% to 15%, or 9% to 12% by weight of a chelant, wherein the chelant is a metal-pyridine oxide complex or a metal phosphonate complex that is co-ordinately bonded to one or more metal ions.

The metal in the metal-phosphonate complex or metal pyridine oxide complex is selected from the group consisting of iron, copper and zinc, preferably zinc. However, it will be understood by one skilled in the art that other metals can be selected according to the Irving Williams Series. Without wishing to be bound by theory, according to Iriving Williams Series, a more stable complex can be formed between phosphonate or pyridine oxide and metal ions having smaller ionic radius. For example, $Fe^{3+}$ has a radius of 0.64 A, which is smaller than $Cu^{2+}$ which has a radius of 0.73 A, and which is in turn smaller than that of $Zn^{2+}$ 0.74 A. Thus, this might help to explain why there can be pyrithione discoloration in ZPT-containing bar soaps in the presence of other transition metal sources (e.g., copper and iron).

The present invention also relates to low moisture solid concentrate compositions due to the introduction of water by ZPT. Therefore, more ZPT in the concentrate composition raises the water content of the concentrate composition so that it can become sticky and challenging to process. Preferably, by limiting the water level to, e.g., 0% to 10%, alternatively 3% to 10%, alternatively 0% to 5%, low moisture noodles would allow for higher ZPT concentration. The additional benefit of having low water level means that less or no preservative is required to be added to the concentrate composition.

One important advantage of the concentrate composition is that it eliminates the need for special equipment to manufacture the concentrate at every production site. This can be important in light of cost considerations. However, as noted above, by introducing higher levels of ZPT there is the potential stickiness issue delivered by higher concentrations of ZPT and associated water. The inventors have surprisingly discovered that a solid concentrate composition comprising: (a) from 5% to 25% by weight of a ZPT; and (b) from 8% to 85% by weight of at least one surfactant, wherein the solid concentrate composition has a penetration hardness of between 20 N and 50 N according to the test method as described herein, avoids, or at least mitigates, aid to reduce and/or eliminate the stickiness problem.

Zinc Pyrithione (ZPT)

Preferably, but not necessarily, ZPT is present in the concentrate composition as a spherical or platelet form, while the ZPT particles have an average size of up to about 20 microns, more preferably up to about 10 microns, even more preferably up to about 5 microns, and most preferably up to about 2.5 microns to about 0.3 microns, 0.2 microns or 0.1 microns, as determined according to light scattering based particle size measurements as known to those skilled in the art using equipment, such as, Horiba LA910 particle size apparatus or its equivalent. Alternatively, ZPT is present in a particulate form that is non-platelet and non-spherical, having a configuration selected from the group consisting of rods, needles, cylinders, cones, ellipsoids, prisms, parallelepipeds, pyramids, tetrahedrons, hexahedrons, octahedrons, dodecahedrons, icosahedrons, and combinations thereof, as described by U.S. Pat. No. 6,242,007.

ZPT may be incorporated into the concentrate composition of the present invention in the form of a powder or slurry. For example, ZPT can be added to the concentrate composition as a powder, then only one dust handling apparati is needed for one manufacturing line. Thereafter, the manufacturing process would not require any other manufacturing line to require the special dust handling machinery and thereby minimizing capital expenditures. In a preferred embodiment, the ZPT included in the solid concentrate composition is a dry powder ZPT in platelet particle form ("platelet ZPT"). The platelet ZPT can have a median particle diameter of, for example, from about 0.05 to about 10 microns, alternatively from about 0.1 to about 8 microns, and alternatively from about 0.2 to about 5 microns, and alternatively about 3 microns. The platelet ZPT can also have a thickness of, for example, from about 0.1 to about 15 microns, alternatively from about 0.5 to about 1 micron, alternatively from about 0.6 to about 0.8 microns, and alternatively from about 0.6 to about 0.7 microns, as described in U.S. Patent Publication 2012/0219610. The platelet ZPT thickness can be measured microscopically using an electron scanning microscope as known to those skilled in the art, or alternatively measured from microphotographs.

ZPT as used in the present invention may be made by reacting 1-hydroxy-2-pyridinethione (i.e., pyrithione acid) or a soluble salt thereof with a zinc salt (e.g., $ZnSO_4$) to form a ZPT precipitate, as illustrated by the disclosures of U.S. Pat. No. 2,809,971, or processed into platelet ZPT using, for example, sonic energy as illustrated by U.S. Pat. No. 6,682,724, or by any other methods currently known in the art.

Solid concentrate compositions of the present invention can be used in order to deliver a less expensive product. The ZPT level in the concentrate composition of the present invention is from 5% to 25% by weight of the ZPT. In an embodiment, the level is from 6% to 8% by weight of the ZPT. Higher levels of ZPT in the concentrate composition is beneficial because less of the concentrate composition is required thus permitting for a less expensive product. Without wishing to be bound by theory, higher ZPT activity in the ZPT raw material used in the concentrate composition would be advantageous because lower amounts of the ZPT would be required thereby introducing less water, so that higher ZPT level can be present in the concentrate composition.

In an embodiment, the solid concentrate composition can be used to form bar soaps. Preferably, but not necessarily, the bar soaps of the present invention contain ZPT in the amount ranging from about 0.01% to about 10% by total weight of such compositions. More preferably, such bar soaps contain from about 0.1% to about 5.0% ZPT by total weight.

Metal-Phosphonate Complex

In an embodiment, the solid concentrate compositions of the present invention may comprise a metal-phosphonate complex, which comprises one or more phosphonate chelants that are co-ordinately bonded to one or more metal ions. The metal is selected from the group consisting of iron, copper and zinc. However, it will be understood by one skilled in the art that other metals can be selected according to the Irving Wiliams Series, which refers to the relative stability of complexes formed by a metal ion.

In a preferred embodiment, the metal is zinc. Such zinc-phosphonate complex has a surprising and unexpected effect on stabilizing the ZPT against potential transchelation by iron chelating iron that may be present and improving the discoloration resistance of the ZPT-containing concentrate compositions and/or bar soaps made from such concentrate compositions, which is demonstrated by a significant increase in its resistance to laboratory-induced discoloration in comparison with control samples containing ZPT only or with uncomplexed phosphonate chelant.

In a particularly preferred embodiment of the present invention, the phosphonate chelant comprises one or more functional groups of the formula (I):

wherein $R_1$ is a linear, branched or cyclic, saturated or unsaturated, substituted or unsubstituted $C_1$-$C_{20}$ hydrocarbon group, and wherein $R_2$ and $R_3$ are independently selected from the group consisting of hydrogen and $R_1$. Preferably, both $R_2$ and $R_3$ are hydrogen.

Exemplary phosphonate chelants that are suitable for practice of the present invention include, but are not limited to: 2-aminoethyl phosphoric acid (AEP), N-phosphonomethyl aminodiacetic acid (PMIDA), 1-hydroxyethane-1,1-diphosphonic acid (HEDP), amino tris(methylene phosphonic acid) (ATMP), ethylenediamine tetra(methylene phosphonic acid) (EDTMP), diethylenetriamine penta(methylene phosphonic acid) (DTPMP), phytic acid, and nitrilourimethylene phosphonic acid (NTP).

A representative species of phosphonate chelant that is particularly useful for the practice of the present invention is HEDP, which has the chemical structure of formula (II):

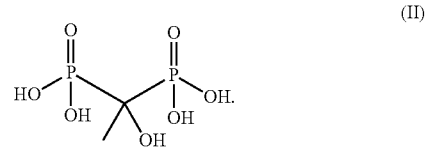

As a chelant, HEDP is capable of forming coordination complexes with transition metal ions in solution. Specifically, one or more HEDP can be bonded to one or more zinc ions to form a Zn-HEDP complex, which is a particularly preferred Zn-phosphonate compound for the present invention. It is important to note that zinc ions may be able to form various complexes with HEDP, with one or more HEDP attached to one or more zinc ions. In solution, zinc ions and HEDP may undergo speciation to form a mixture of different complex species, and the relative concentration of such complex species can vary depending on the chemical environment they are in, such as pH and the presence of other metal ions or chelant species. For ease of reference, all such complex species are herein referred to as the "Zn-HEDP complex," regardless of the actual number of HEDP or zinc ions included, and they are all included within the scope of the present invention.

The amount of zinc-phosphonate complex present in the concentrate compositions of the present invention may range from about 1% to about 15% by total weight of such concentrate compositions. More preferably, such concentrate compositions contains from about 2% to about 10% zinc-phosphonate complex, still more preferably from about 4% to about 8% or from about 4.5% to about 7% by total weight.

The zinc-phosphonate complex as used in the present invention can be pre-formed by reacting the phosphonate chelant with zinc oxide or a soluble zinc salt, such as $ZnSO_4$, $ZnCl_2$, or a mixture thereof. The reactant solution can then be added into the concentrate compositions.

Alternatively, the zinc-phosphonate complex can be formed in situ by directly adding the precursors, i.e., the phosphonate chelant and zinc oxide or the soluble zinc salt, into the concentrate compositions, which will directly complex with each other in the concentrate compositions. The phosphonate compound and zinc oxide or zinc salt can be added either in dry power form or pre-dissolved/dispersed in a solution.

In another embodiment, the phosphonate chelant comprises a zinc-phosphonate complex and wherein the molar ratio of zinc to the phosphonate chelant ranges from 2:1 and 4:1. In yet another embodiment, the molar ratio of ZPT to zinc-phosphonate complex in the concentrate compositions of the present invention is preferably ranging from 1.2:1 to 3:1, respectively, more preferably from 1.5 to 2:1.

Metal-Pyridine Oxide Complex

In another embodiment, the concentrate compositions of the present invention may comprise a metal-pyridine oxide complex, which comprises a pyridine oxide compound that is co-ordinately bound to a metal ion. In an embodiment, the metal is selected from the group consisting of iron, copper and zinc. However, it will be understood by one skilled in the art that other metals can be selected according to the Irving Wiliams Series, which refers to the relative stability of complexes formed by a metal ion.

In a preferred embodiment, the metal is zinc. Such zinc-pyridine oxide complex has a surprising and unexpected effect on the discoloration resistance of the ZPT-containing bar soap compositions, which is demonstrated by a significant increase in its resistance to laboratory-induced discoloration in comparison with control samples containing ZPT only. According to this embodiment, the zinc-pyridine oxide complex acts in synergy with ZPT to improve the anti-microbial effect of the bar soaps made from the concentrate compositions, especially against gram-positive bacteria. It may further provide an extended shelf life for such concentrate compositions and/or bar soaps made from such concentrate compositions.

In a particularly preferred embodiment of the present invention, the pyridine oxide compound has the chemical structure of formula (III):

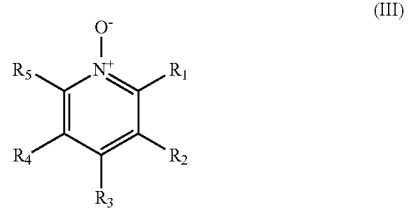

wherein $R_1$, $R_2$, $R_3$, $R_4$, and $R_5$ are each independently selected from the group consisting of H, OH, a halogen (such as F, Cl, Br, and I), NO, $NO_2$, and a $C_1$-$C_{12}$ organic group that is linear or branched, saturated or unsaturated, substituted or unsubstituted.

More preferably, $R_1$ or $R_5$ is OH, and $R_2$, $R_3$, and $R_4$ is each independently selected from the group consisting of H, OH, and a $C_1$-$C_8$ alkyl, alkylene, alkyne, or aryl group. It is to be understood that various potential and actual resonate structures of the pyridine oxides may exist (i.e., the bond between the N and O atoms and/or the bond between the neighboring C atom and —OH group may resonate between a single bond and a double bond), for example, according to the chemical structures of formula (IV):

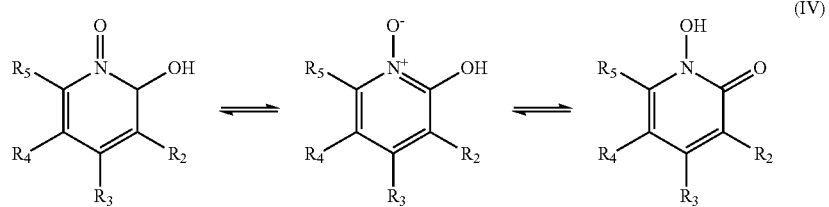

It is intended that all of the reasonable resonate structures are meant to be represented by the formula (IV) hereinabove and are thereby included within the scope of the present invention.

Useful pyridine oxide compounds that can be employed in the practice of the present invention include 2-hydroxypyridine-N-oxide ("HPNO"), N-hydroxy-6-octyloxy-2(1H)-pyridone, ciclopirox olamine, piroctone olamine, and derivatives thereof.

A representative species of pyridine oxide compounds that is particularly useful for the practice of the present invention is 2-hydroxypyridine-N-oxide ("HPNO"), which has the chemical structure of formula (V):

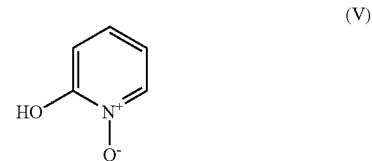

As a bidentate chelant, HPNO is capable of forming co-ordination complexes with transition metal ions in solution. Specifically, two HNPO can be bound to one zinc ion to form a Zn-HNPO complex with the chemical structure of formula (VI):

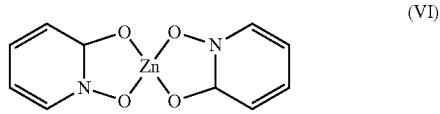

Zn-HPNO is a particularly preferred Zn-pyridine oxide compound for the present invention. It is important to note that zinc ions can form various complexes with HPNO, with one, two, three, or even four HPNO attached to one zinc ion, although only the complex with two HPNO attached to one zinc ion as shown by formula (VI) has a neutral charge. In solution, zinc ions and HPNO may undergo speciation to form a mixture of different complex species, and the relative concentration of such complex species can vary depending on the chemical environment they are in, such as pH and the presence of other metal ions or chelant species. For ease of reference, all such complex species are herein referred to as the "Zn-HPNO complex," regardless of the actual number of HPNO included, and they are all included within the scope of the present invention.

Various derivatives or salts of HPNO with similar chemical structure can also form similar complexes with Zn ions and are therefore also useful for the practice of the present invention. Exemplary HPNO derivatives or salts include, but are not limited to: 6-hydroxy-3-pyridine sulfonic acid, 1-oxide (CAS 191672-18-1); 2-hydroxy-4-pyridine carboxylic acid, 1-oxide (CAS 13602-64-7); 5-ethoxy-2-pyridinol, 2-acetate, 1-oxide (CAS 51984-49-7); 1-(3-hydroxy-2-oxido-4-isoquinolinyl)-ethanone (CAS 65417-65-4); 6-hydroxy-3-pyridine carboxylic acid, 1-oxide (CAS 90037-89-1); 2-methoxy-4-quinolinecarbonitrile, 1-oxide (CAS 379722-76-6); 2-pyridine carboxylic acid, 6-hydroxy-, 1-oxide (CAS 1094194-45-2); 3-pyridine carboxylic acid, 2-hydroxy-, 1-oxide (CAS 408538-43-2); 2-pyridinol, 3-nitro-, 1-oxide (CAS 282102-08-3); 3-pyridine propanenitrile, 2-hydroxy-, 1-oxide (193605-60-6); 3-pyridine ethanol, 2-hydroxy-, 3-acetate, 1-oxide (CAS 193605-56-0); 2-pyridinol, 4-bromo-, 1-oxide (CAS 170875-41-9); 2-pyridinol, 4,6-dibromo-, 2-acetate, 1-oxide (CAS 170875-40-8); 2-pyridinol, 4,6-dibromo, 1-oxide (CAS 170875-38-4); 2-pyridinol, 4-(2-aminoethyl)-, 1-oxide (CAS 154403-93-7); 2-pyridinol, 5-(2-aminoethyl)-, 1-oxide (CAS 154403-92-6); 3-pyridine propanoic acid, α-amino-6-hydroxy-, 1-oxide (CAS 134419-61-7); 2-pyridinol, 3,5-dimethyl, 1-oxide (CAS 102074-62-4); 2-pyridinol, 3-methyl-, 1-oxide (CAS 99969-07-0); 2-pyridinol, 3,5-dinitro, 1-oxide (CAS 98136-47-1); 2-pyridinol, 3,5-dibromo-, 1-oxide (CAS 98136-29-9); 2-pyridinol, 4-methyl-6-(2-methylpropyl)-, 1-oxide (CAS 91408-77-4); 2-pyridinol, 3-bromo-4,6-dimethyl-, 1-oxide (CAS 91408-76-3); 2-pyridinol, 4,5,6-trimethyl-, 1-oxide (CAS 91408-75-2); 2-pyridinol, 6-heptyl-4-methyl-, 1-oxide (CAS 91408-73-0); 2-pyridinol, 6-(cyclohexylmethyl)-4-methyl-, 1-oxide (CAS 91408-72-9); 2-pyridinol, 6-bromo-, 1-oxide (CAS 89284-00-4); 2-pyridinol, 5-bromo-, 1-oxide (CAS 89283-99-8); 2-pyridinol, 3,5-dichloro-4,6-difluoro-, 1-oxide (CAS 33693-37-7); 2-pyridinol, 3,4,5,6-tetrachloro-, 1-oxide (CAS 32835-63-5); 2-pyridinol, 6-methyl-, 1-oxide (CAS 14420-62-3); 2-pyridinol, 5-nitro-, 1-oxide (CAS 14396-03-3); 2-pyridinol, 4-methyl-5-nitro-, 1-oxide (CAS 13602-77-2); 2-pyridinol, 4-chloro-5-nitro-, 1-oxide (CAS 13602-73-8); 2-pyridinol, 4-chloro-, 1-oxide (CAS 13602-65-8); 2-pyridinol, 4-nitro-, 1-oxide (CAS 13602-63-6); and 2-pyridinol, 4-methyl-, 1-oxide (CAS 1952-64-3), and mixtures thereof. These compounds are commercially available from, for example, Sigma-Aldrich (St. Louis, Mo.) and/or Aces Pharma (Branford, Conn.).

The amount of zinc-pyridine oxide complex present in the concentrate compositions of the present invention may range from about 0.01% to about 15% by total weight of such compositions. More preferably, such concentrate compositions contains from about 0.05% to about 10% zinc-pyridine oxide complex, still more preferably from about 0.1% to about 7% or from about 0.5% to about 5%, alternatively from 1% to 3%, alternatively combinations thereof, by total weight.

The zinc-pyridine oxide complex as used in the present invention is present in the concentrate compositions as particles, which can be pre-formed by reacting the pyridine oxide compound with a soluble zinc salt, such as $ZnSO_4$, $ZnCl_2$, or a mixture thereof, thereby forming an insoluble precipitate. The term "soluble" as used herein refers to a solubility of at least 0.01 gram per liter in an aqueous solution at 25° C. The precipitate is then processed into dry powders or used to form a colloidal or slurry composition containing particulates dispersed in a solution, which can be subsequently added into the concentrate compositions.

Alternatively, the particles of zinc-pyridine oxide complex can be formed in situ by directly adding the precursors, i.e., the pyridine oxide compound and the soluble zinc salt, into the concentrate compositions, which will complex with each other in the concentrate compositions to form particles. The pyridine oxide compound and zinc salt can be added either in dry power form or pre-dissolved in a solution.

The particles of zinc-pyridine oxide complex are characterized by an average particle size ranging from about 0.05 micron to about 5,000 microns, preferably from about 0.1 micron to about 2,000 microns, more preferably from about 0.2 micron to about 1,000 microns, and most preferably from about 1 micron to about 600 microns.

The particle size of the zinc-pyridine oxide complex can be readily controlled by modulating the homogenization rate when mixing the soluble zinc salt and the pyridine oxide compound, i.e., the faster the homogenization, the slower the particle growth rate, and consequently the smaller the particles. The particles can further be processed by milling or grinding to achieve a more uniform particle size distribution.

In another embodiment, wherein the chelant is a zinc-pyridine oxide complex and wherein the molar ratio of zinc to the zinc-pyridine oxide complex ranges from 5:1 to 1:5. In yet another embodiment, the molar ratio of ZPT to Zn-pyridine oxide complex in the concentrate compositions of the present invention is preferably ranging from about 5:1 to about 1:10, more preferably from about 4:1 to about 1:6, still more preferably from about 3:1 to about 1:2, and most preferably about 2:1 to about 1:1.

pH and pH Adjusting Agents

Stability of concentrate compositions is important, and can be impacted by pH. The concentrate compositions are preferably characterized by a pH value ranging from 4 to 11 when dispersed in a 1 wt % aqueous solution. More preferably, the concentrate compositions have a pH range of 4 to 9 or 9 to 11, even more preferably from 9.9 to 10.7, yet even more preferably from 10.1 to 10.6, and most preferably from 10.1 to 10.4.

In an embodiment, the solid concentrate composition of the present has a pH value ranging from 9 to 11 when dispersed in a 1 wt % aqueous solution. Of this embodiment, the composition comprises a $C_6$-$C_{22}$ fatty acid, $C_8$-$C_{22}$ fatty alcohol, or mixtures thereof. In another embodiment, the solid concentrate composition of the present has a pH value ranging from 4 to 9 when dispersed in a 1 wt % aqueous solution. Of this embodiment, the composition comprises a $C_8$-$C_{18}$ fatty acid, $C_8$-$C_{20}$ fatty alcohol or mixtures thereof.

This pH range is particularly beneficial for maintaining the dissolution equilibrium of ZPT and the Zn-phosphonate complex or Zn-pyridine oxide complex in the concentrate compositions, and can thereby extend or maximize the shelf life of the concentrate composition. The pH of the concentrate compositions of the present invention can be readily adjusted or modulated by various mechanisms. For example, the pH modulation can be achieved by adjusting the amounts of raw materials used for soap-making, i.e., fats, oils, and base materials such as sodium or potassium hydroxide, so as to reach a final concentrate composition with the desired pH value. For another example, the pH modulation can be achieved using a pH buffering agent, such as potassium carbonate or zinc carbonate. Further, the pH modulation can also be achieved through employment of an acidic pH adjusting agent.

In a preferred, but not necessary, embodiment of the present invention, the pH modulation is achieved by using an acid. Not all acids are suitable for practice of the present invention, and it has been observed that certain acids will aggravate the ZPT discoloration, while other acids help to reduce or alleviate it.

Particularly, it has been discovered that acids having an acid dissociation constant (pKa) of no more than 10 measured at a temperature of 25° C. and an ferric ion-complex stability constant (log K1) of no more than 8 measured at a temperature of 25° C. and an ion strength of 0.1M are particularly effective in reducing or alleviating the ZPT discoloration problem. The term "ferric ion-complex stability constant" as used herein refers to the stability constant of a complex formed between the acid of interest and ferric ions. Preferably, the acids are characterized by a pKa of no more than 8 and a log K1 of no more than 6 measured under the same conditions as described hereinabove. More preferably, the acids are characterized by a pKa of no more than 6 and a log K1 of no more than 4, as measured under the same conditions as described hereinabove.

Most preferably, acids used for practice of the present invention are selected from the group consisting of sulfuric acid, nitric acid, phosphoric acid, lactic acid, formic acid, acrylic acid, pyruvic acid, malonic acid, glyceric acid, glycine, L-alanine, β-alanine, methylglycine, maleic acid, dihydroxytartaric acid, creatinine, asparagine, N-glycylglycine, butanoic acid, betaine, valine, N-propylglycine, 5-aminopentanoic acid, trimethylacetic acid, pentanoic acid, benzoic acid, $C_6$-$C_{22}$ fatty acids, and combinations thereof. Fatty acids are particularly preferred acidic pH adjusting agents for the practice of the present invention.

Any fatty acids with total carbon numbers ranging from $C_6$ to $C_{22}$ can be used for the practice of the present invention. Exemplary fatty acids include, but are not limited to: caproic acid, caprylic acid, capric acid, lauric acid, myristic acid, palmitic acid, stearic acid, arachidic acid, behenic acid, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, and the like. Particularly useful fatty acids for the practice of the present invention are saturated or unsaturated fatty acids with total carbon numbers ranging from $C_{12}$ to $C_{22}$, such as, for example, lauric acid, myristic acid, palmitic acid, stearic acid, palmitoleic acid, oleic acid, and behenic acid.

In contrast, certain acids, such as hydrochloric acid, citric acid, aspartic acid, picolinic acid, 4-pyridinecarboxylic acid, 3-pyridinecarboxylic acid, tartaric acid, oxalic acid and glutamic acid, have been found to further aggravate the ZPT discoloration problem. It is therefore desirable, although not necessary, to formulate the concentrate compositions of the present invention with as little of these types of acids as possible. Preferably, the concentrate compositions of the present invention are substantially free of hydrochloric acid, citric acid, aspartic acid, picolinic acid, 4-pyridinecarboxylic acid, 3-pyridinecarboxylic acid, tartaric acid, oxalic acid, glutamic acid, or any combination thereof.

Reducing Agents

The concentrate compositions of the present invention may optionally comprise one or more reducing agents, which are preferably, but not necessarily, selected from sterically hindered phenols. Such reducing agents can further improve the discoloration resistance of the concentrate compositions, and/or soap bars formed therefrom, as well as extending the shelf life thereof.

Sterically hindered phenolic reducing agents suitable for the use of the present invention are characterized by a molecular weight above 500 Da. Preferred examples include 2,4-dimethyl-6-octyl-phenol; 2,6-di-t-butyl-4-methyl phenol (i.e., butylated hydroxy toluene); 2,6-di-t-butyl-4-ethyl phenol; 2,6-di-t-butyl-4-n-butyl phenol; 2,2'-methylenebis (4-methyl-6-t-butyl phenol); 2,2'-methylenebis(4-ethyl-6-t-butyl phenol); 2,4-dimethyl-6-t-butyl phenol; 4-hydroxymethyl-2,6-di-t-butyl phenol; n-octadecyl-beta(3,5-di-t-butyl-4-hydroxyphenyl)propionate; 2,6-dioctadecyl-4-methyl phenol; 2,4,6-trimethyl phenol; 2,4,6-triisopropyl phenol; 2,4,6-tri-t-butyl phenol; 2-t-butyl-4,6-dimethyl phenol; 2,6-methyl-4-didodecyl phenol; tris(3,5-di-t-butyl-4-hydroxy isocyanurate, and tris(2-methyl-4-hydroxy-5-t-butylphenyl) butane.

More preferred are pentaerythrityl tetra-di-t-butyl hydroxyhydrocinnamate (Tinoguard® TT, BASF); octadecyl-3,5-di-t-butyl-4-hydroxy-hydrocinnamate (NAUGARD 76, Uniroyal Chemical; IRGANOX 1076, Ciba-Geigy); tetrakis+methylene(3,5-di-t-butyl-4-hydroxy-hydrocinnamate)}methane (NAUGARD 10, Uniroyal Chemical; IRGANOX 1010, Ciba-Geigy); 2,2'-oxamido bis+ethyl-3-(3,5-di-t-butyl-4-hydroxyphenyl)}propionate (NAUGARD XL-1, Uniroyal Chemical); 1,2-bis(3,5-di-t-butyl-4-hydroxyhydrocinnamoyl)hydrazine (IRGANOX MD 1024, Ciba-Geigy); 1,3,5-tris(3,5-di-t-butyl-4-hydroxybenzyl)-s-triazine-2,4,6 (1H,3H,5H)trione (IRGANOX 3114, Ciba-Geigy); 1,3,5-tris(4-t-butyl-3-hydroxy-2,6-dimethylbenzyl)-s-triazine-2,4,6-(1H,3H,5H)trione (CYANOX 1790, American Cyanamid Co.); 1,3,5-trimethyl-2,4,6-tris(3,5-di-t-butyl-4-hydroxybenzyl)benzene (ETHANOX 330, Ethyl Corp.); 3,5-di-t-butyl-4-hydroxyhydrocinnamic acid triester with 1,3,5-tris(2-hydroxyethyl)-5-triazine-2,4,6(1H,3H,5H)-trione, and bis(3,3-bis(4-hydroxy-3-t-butylphenyl)butanoic acid)glycolester.

Most preferred reducing agents for the practice of the present invention are pentaerythrityl tetra-di-t-butyl hydroxyhydrocinnamate, which is commercially available under the trade name of Tinogard® TT from BASF (Monheim, Germany).

The amount of reducing agent present in the concentrate compositions of the present invention may range from about 0.001% to about 5% by total weight of such concentrate compositions. More preferably, such concentrate compositions contains from about 0.01% to about 1% of the reducing agent, and most preferably from about 0.02% to about 0.5%, by total weight of such concentrate compositions.

Soap Surfactants

The concentrate compositions of the present invention will typically comprise a soap surfactant, or in short "soap", in an amount ranging from about 8%, 10%, 15% or 20% to about 85%, 80%, 75%, or 70%. The term "soap" is used herein in its popular sense, i.e., the alkali metal or alkanol ammonium salts of alkane- or alkene monocarboxylic acids. Sodium, magnesium, potassium, calcium, mono-, di- and tri-ethanol ammonium cations, or combinations thereof are suitable for purposes of the present invention. In general, sodium soaps are used in the concentrate compositions of this invention, but from about 1% to about 25% of the soap may be ammonium, potassium, magnesium, calcium or a mixture of these soaps. The soaps useful herein are the well known alkali metal salts of alkanoic or alkenoic acids having about 12 to 22 carbon atoms, preferably about 12 to about 18 carbon atoms. They may also be described as alkali metal carboxylates of alkyl or alkene hydrocarbons having about 12 to about 22 carbon atoms.

It can be preferred to use soaps having the fatty acid distribution of tallow and vegetable oil (i.e., "fatty acid soaps"). More preferably, the vegetable oil is selected from the group consisting of peanut oil, grapeseed oil, corn oil, olive oil, palm oil, coconut oil, palm kernel oil, palm oil stearine, and hydrogenated rice bran oil, or mixtures thereof, since these are among the more readily available fats. Especially preferred are palm oil stearine, palm kernel oil, and/or coconut oil. The proportion of fatty acids having at least 12 carbon atoms in coconut oil soap is about 85%. This proportion will be greater when mixtures of coconut oil and fats such as tallow, palm oil, or non-tropical nut oils or fats are used, wherein the principal chain lengths are $C_{16}$ and higher. A preferred soap is sodium soap having a mixture of about 50% tallow, 30% palm oil stearine, and 20% palm kernel oil or coconut oil.

Soaps may be made by the classic kettle boiling process or modern continuous soap manufacturing processes wherein natural fats and oils such as tallow or coconut oil or their equivalents are saponified with an alkali metal hydroxide using procedures well known to those skilled in the art. Alternatively, the soaps may be made by neutralizing fatty acids, such as lauric ($C_{12}$), myristic ($C_{14}$), palmitic ($C_{16}$), or stearic ($C_{18}$) acids with an alkali metal hydroxide or carbonate.

Synthetic Surfactants

Synthetic surfactants can be utilized in the present concentrate compositions, either in combination with or in place of the soap surfactants described hereinabove, to further improve the lathering properties of the bar soap during use. When a majority of the surfactants in the concentrate compositions of the present invention are synthetic surfactants rather than soap surfactants, the pH value of the concentrate compositions can be readily broaden to the relatively lower pH range of 7 to 9. In certain embodiments, the pH value of such concentrate compositions may approach the neutral pH range of 6 to 8, which is particularly beneficial because the resulting bar soaps manufactured from the concentrate compositions are more gentle and less irritating to the skin.

The synthetic surfactants useful in this invention include anionic, amphoteric, nonionic, zwitterionic, and cationic surfactants. Synthetic surfactants are typically incorporated in the present concentrate compositions at a level of from about 0.1% to about 90%, preferably from about 0.5% to about 85%, and more preferably from about 0.75% to about 50%, by weight of the concentrate composition.

Examples of anionic surfactants include but are not limited to alkyl sulfates, anionic acyl sarcosinates, methyl acyl taurates, N-acyl glutamates, acyl isethionates, alkyl ether sulfates, alkyl sulfosuccinates, alkyl phosphate esters, ethoxylated alkyl phosphate esters, trideceth sulfates, protein condensates, mixtures of ethoxylated alkyl sulfates and the like. Alkyl chains for these surfactants are $C_8$-$C_{22}$, preferably $C_{10}$-$C_{18}$ and, more preferably, $C_{12}$-$C_{14}$ alkyls.

Zwitterionic surfactants can be exemplified by those which can be broadly described as derivatives of aliphatic quaternary ammonium, phosphonium, and sulfonium compounds, in which the aliphatic radicals can be straight chain or branched and wherein one of the aliphatic substituents contains from about 8 to 18 carbon atoms and one contains an anionic water-solubilizing group, for example, carboxy, sulfonate, sulfate, phosphate, or phosphonate. Examples include: 4-[N,N-di(2-hydroxyethyl)-N-octadecylammonio]-butane-1-carboxylate; 5-[S-3-hydroxypropyl-S-hexadecyl-sulfonio]-3 hydroxypentane-1-sulfate; 3-[P,P—P-diethyl-P 3,6,9 trioxatetradecyl-phosphonio]-2-hydroxypropane-1-phosphate; 3-[N,N-dipropyl-N-3-dodecoxy-2-hydroxypropylammonio]-propane-1-phosphonate; 3-(N,N-di-methyl-N-hexadecylammonio)propane-1-sulfonate; 3-(N,N-dimethyl-N-hexadecylammonio)-2-hydroxypropane-1-sulfonate; 4-(N,N-di(2-hydroxyethyl)-N-(2 hydroxydodecyl)ammonio]-butane-1-carboxylate; 3-[S-ethyl-S-(3-dodecoxy-2-hydroxypropyl)sulfonio]-propane-1-phosphate; 3-(P,P-dimethyl-P-dodecylphosphonio)-propane-1-phosphonate; and 5-[N,N-di(3-hydroxypropyl)-N-hexadecylammonio]-2-hydroxy-pentane-1-sulfate.

Examples of amphoteric surfactants which can be used in the concentrate compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate; N-alkyl-taurines, such as the one prepared by reacting dodecylamine with sodium isethionate according to the teaching of U.S. Pat. No. 2,658,072; N-higher alkyl aspartic acids, such as those produced according to the teaching of U.S. Pat. No. 2,438,091; and the products sold under the trade name "Miranol" and described in U.S. Pat. No. 2,528,378. Other amphoterics such as betaines are also useful in the present composition. Examples of betaines useful herein include the high alkyl betaines such as coco dimethyl carboxymethyl betaine, lauryl dimethyl carboxy-methyl betaine, lauryl dimethyl alpha-carboxyethyl betaine, cetyl dimethyl carboxymethyl betaine, lauryl bis-(2-hydroxyethyl)carboxy methyl betaine, stearyl bis-(2-hydroxypropyl)carboxymethyl betaine, oleyl dimethyl gamma-carboxypropyl betaine, lauryl bis-(2-hydro-xypropyl)alpha-carboxyet-hyl betaine, etc. The sulfobetaines may be represented by coco dimethyl sulfopropyl betaine, stearyl dimethyl sulfopropyl betaine, amido betaines, amidosulfobetaines, and the like.

Examples of suitable cationic surfactants include stearyldimenthylbenzyl ammonium chloride; dodecyltrimethylammonium chloride; nonylbenzylethyldimethyl ammonium nitrate; tetradecylpyridinium bromide; laurylpyridinium chloride; cetylpyridinium chloride; laurylpyridinium chloride; laurylisoquinolium bromide; ditallow(Hydrogenated)dimethyl ammonium chloride; dilauryldimethyl ammonium chloride; and stearalkonium chloride; and other cationic surfactants known in the art.

Nonionic surfactants useful in this invention can be broadly defined as compounds produced by the condensation of alkylene oxide groups (hydrophilic in nature) with an organic hydrophobic compound, which may be aliphatic or alkyl aromatic in nature.

A preferred synthetic surfactant for use in the present compositions is sodium laureth-3 sulfate. Sodium laureth sulfate tends to provide excellent lathering properties, especially when combined with sodium tripolyphosphate as the inorganic salt in the concentrate compositions.

In an embodiment, the solid concentrate compositions of the present invention comprises surfactant selected from the group consisting of primary alcohol sulfates, alpha olefin sulfonates, acyl isethionates and mixtures thereof.

Other Ingredients

During the soap making process, the concentrate compositions can be mixed with additional ingredients such as, for example, inorganic salts (especially inorganic zinc salts, such as zinc carbonate, zinc sulfate, zinc nitrate, zinc fluoride, zinc chloride, zinc borate, and the like as well as zinc oxide). A particularly preferred inorganic salt is zinc carbonate. In a particularly preferred embodiment of the present invention, the concentrate compositions can be used to form bar soaps containing zinc carbonate at an amount ranging from about 0.01% to about 5%, more preferably from about 0.1% to about 3%, and most preferably from about 1% to about 2% by total weight of the composition. Zinc carbonate provided at such an amount is particularly effective in reducing or removing malodor.

The concentrate compositions of the present invention may further be mixed with one or more optional ingredients selected from the group consisting of: structurants, such as raw starch, pregelatinzed starch, carboxymethyl cellulose, polyacrylate polymer, Carbopol, carregeenan, xanthan gum, polyethylene glycol, polyethylene oxide, and the like; free fatty acids, such as those derived from tallow, coconut, palm and palm kernel; humectants; cationic polymers, such as cationic polysaccharides, cationic polyalkylene imines, cationic hydroxyethyl cellulose, and the like; brighteners; fillers, such as silica, talc, and the like; perfumes; sequestering agents; coloring agents; opacifiers and pearlizers, such as titanium dioxide.

All of these are useful in enhancing the appearance, smell or other cosmetic/sensory properties of the products made from the concentrate compositions. For example, with bar soaps, the appearance can be transparent, translucent, or opaque, and the color thereof can be white, off-white, cream, yellow, pink, red, green, purple, blue and black. In one embodiment, the bar soaps is opaque with a white or off-white color.

Preparation Methods

Concentrate compositions of the present invention can be made via a number of different processes. In an aspect, the present invention is directed to a method of manufacturing a solid concentrate composition, comprising the steps of: (a) forming a mixture that comprises from 5% to 25% by weight of a zinc pyrithione (ZPT), and from 8% to 85% by weight of at least one surfactant by total weight of the mixture; and (b) shaping the mixture to form a solid concentrate composition. In an embodiment of this method, wherein the solid concentrate composition has a penetration hardness of between 20 N and 50 N according to the test method as disclosed herein.

Preferably, the concentrate compositions of the present invention can be made by the following process. First, all the ingredients, such as the surfactant, ZPT (either as solid powder material or an aqueous dispersion), and fillers, are added into an amalgamator and blended for approx. 5 to 10 mins to form coated pellets. Then the coated pellets from the amalgamator are refined by high shearing force, either in the refining plodder or in the roll mill, to achieve good homogeneity. The resultant mixture from then is extruded in a plodder and shaped into pellets by the pore plate at the plodder outlet.

Bar soaps made from the concentrate composition, as described above, can be made via a number of different processes. In another aspect, the present invention is directed to a method of forming a bar soap, comprising the steps of: (a) forming a mixture by diluting a solid concentrate composition that comprises from 5% to 25% by weight of a zinc pyrithione (ZPT), and from 8% to 85% by weight of at least one surfactant by total weight of the mixture; and (b) shaping the mixture to form a solid concentrate composition. In an embodiment of this method, wherein the solid concentrate composition has a penetration hardness of between 20 N and 50 N according to the test method as disclosed herein.

Preferably, the present compositions are made via a process that involves milling, resulting in milled bar soap compositions. A typical milling process of manufacturing a bar soap composition includes: (a) a step in which the soap is made through either a continuous process (ConSap or continuous saponification process) or a batch-making process (i.e. neutralization process for hydrolysis fatty acid noodle or kettle process), (b) a vacuum drying step in which the soap is made into soap noodles, (c) an amalgamating step in which the soap noodles are combined with other ingredients of the bar soap composition, (d) a milling step in which a relatively homogeneous mixture is obtained, (e) a plodding step in which the soap mixture is extruded as soap logs and then cut into soap plugs, and (f) a stamping step in which the soap plugs are stamped to yield the finished bar soap composition. The present bar soap can be made using any of the above mentioned manufacturing processes, and the ZPT, the metal-phosphonate complex (or the precursors for in situ forming such complex), and pH adjusting agent, and the reducing agent can be added during the mixing steps of preparing the bar soaps.

Other product forms of the present invention, such as body washes, shower gels, liquid hand soaps, shampoos, facial cleansers, and the like, can be readily formed starting from the concentrate compositions using the conventional mixing or homogenization process known to those skilled in the art.

Test Methods

ZPT Stability

As mentioned hereinabove, zinc pyrithione (ZPT) may undergo transformation upon exposure to oxidizing species, thereby losing its anti-microbial effect over time in environments susceptible to oxidation. Such vulnerability of ZPT to environmental assaults is well known in the art, and various solutions have been proposed to stabilize ZPT with limited success.

It is a surprising and unexpected discovery of the present invention that the above-described metal-phosphonate complex and/or metal-pyridine complex are effective in stabilizing ZPT in concentrate compositions (and bar soaps formed therefrom) to reduce ZPT loss even in harsh chemical environments.

The chemical stability of ZPT is evaluated by an aging test described as follows, so as to determine the percentage loss of ZPT after such aging test. First, a bar soap or concentrate composition containing ZPT is obtained, preferably immediately after it is manufactured. The starting content of ZPT in such bar soap/concentrate composition (in percentage) is measured by method described hereinafter using a portion of the bar soap/concentrate composition, or a companion bar/composition made from the same batch of soap noodle. The bar soap/concentrate composition is weighed (+/−0.01 g), and its starting weight is recorded. Second, the bar soap/concentrate composition is subjected to an aging process, during which the bar soap/concentrate composition is placed inside a sealed water impermeable bag, which is preferably made of polyethylene (PE). The bag containing the bar soap is then left either at room temperature (i.e., about 25° C.), or in a convection oven at an elevated temperature (e.g., 40° C.), for an extended period (e.g., 10 days, 12 days, 14 days, or up to 36 months in certain cases). After the aging, if placed in a convection oven at the elevated temperature, the bar soap/concentrate composition is taken out of the convection oven and allowed to return to room temperature (i.e., 25° C.). The bar soap/concentrate composition is weighed again, and its final weight is recorded. The final content of zinc pyrithione in the bar soap/concentrate composition (in percentage) is measured by the same method as described hereinafter.

Chemical stability of the ZPT is calculated by the following equation to obtain the percentage loss of ZPT:

$$\% \text{ Loss of } ZPT = \left[1 - \frac{\text{Final Weight} \times \text{Final } ZPT \text{ Content } (\%)}{\text{Starting Weight} \times \text{Starting } ZPT \text{ Content } (\%)}\right] \times 100\%,$$

The content of ZPT in bar soap/concentrate compositions is measured herein by an iodine-based titration method, which is described in greater detail in the following sections. The mercapto group in ZPT can be titrated by iodine, which oxidizes it to the disulfide-2,2' dithiobispyridine-1-oxide. If ZPT has already been oxidized or undergone transformation otherwise so that it no longer possesses the mercapto group, it will not be detectable by the iodine-based titration method described hereinafter.

First, a standardized 0.04N iodine solution is prepared. Specifically, anhydrous sodium thiosulphate (with a minimum purity of 99%) is oven-dried for 2 hours at 105° C. and then stored in a dessicator. 0.05 grams (+/−0.0001 g) of the anhydrous sodium thiosulfate is weighed and placed into the 100 ml polypropylene beaker of an autotitrator, and 50 ml of deionized water is added to form a standard solution. The autotitrator used herein is preferably a Mettler DL25 or Mettler DM140-SC titrator with platinum ring electrode, which is commercially available from Mettler Toledo Internantional, Inc. (Switzerland), or an equivalent thereof. The autitrator is set up to titrate the standard sodium thiosulfate solution with the iodine solution that is being standardized. Bubbles are eliminated from the burette of the autotitrator, and titration is commenced. Such procedure is repeated twice more, and the results are averaged to obtain a standardized 0.04N iodine solution. The % relative standard deviation (RSD) should be less than 1% of the average.

Next, standardized 0.01 N and 0.006 N iodine solutions are prepared. Specifically, standardized 0.01 N iodine solution is prepared using 0.10 g (+/−0.0001 g) sodium thiosulphate dissolved in 100 mL deionized water, using 10.0 mL pipetted into the 100 mL autotitrator breaker with 50 mL additional deionized water followed by the titration procedure. Standardized 0.006 N iodine solution is prepared using 3.0 mL of a 0.01 M sodium thiosulphate solution and 40 mL of a solvent (containing 13% v/v hydrochloric acid in 6% v/v butanol), followed by addition of 40 mL of 1:1 hexane/isopropanol. The autotitration procedure is subsequently carried out. The iodine solutions are standardized daily.

The bar soap/concentrate composition whose ZPT content is to be measured is then shredded using a grater and stirred to form a homogenous mixture. 4.00 grams of the shredded soap is weighed and put into a clean, dry beaker of an autotitrator. 75 mL of hot 6% v/v butanol (which was heated in a boiling-water bath) and 5 mL of concentrated HCl (provided at room temperature) are then added into the beaker. The mixture is agitated vigorously so as to fully dissolve all soluble components. The beaker is subsequently placed in the autotitrator, and bubbles are completely eliminated from the burette.

The titration is then initiated and analyzed while the mixture is still warm. The mixture is vigorously agitated during the titration procedure. For compositions with less than 0.2% of ZPT by weight, titration is carried out using the 0.006 N iodine solution. For compositions with higher ZPT concentrations, the initial starting sample weight can be reduced. Titration can be done either manually or by using autotitration procedure by those with skill in the art.

The ZPT content in the bar soap/concentrate composition is calculated as follows:

$$ZPT \text{ Content } (\%) = \frac{\text{Volume of Iodine Solution (ml)} \times N \times 15.88\%}{\text{Sample Weight (g)}},$$

wherein N is the normality of the standardized iodine solution, and wherein 15.88% is a constant that is derived from:

$$15.88\% = \frac{\text{Molecular Weight of } ZPT \times 100\%}{\text{Number of Pyrithione per Molecule} \times 1000 \text{ ml/Liter}} = \frac{371.6 \times 100\%}{2 \times 1000 \text{ ml/Liter}},$$

The above-described procedure is repeated three times for each bar soap composition whose ZPT content is to be measured, and the results are averaged to obtain a final ZPT content in percentage (%) for the specific bar soap/concentrate composition. All chemical reagents employed hereinabove are high-purity reagents obtained from VWR Scientific (Batavia, Ill., USA) or other scientific chemical suppliers.

Water Activity

Water Activity ("Aw") is a measurement of the energy status of the water in a system. It indicates how tightly water is bound, structurally or chemically, within a composition. Water activity ("Aw") is defined as the ratio of the water vapor pressure over a sample (P) to that over pure water ($P_0$):

$$A_W = \frac{P}{P_0}$$

Water activity of a concentrate composition or a bar soap made from the concentrate composition can be measured electronically using a water activity meter with a sealed chamber and an electrical or optical measurement of the headspace. The meter is calibrated against a series of saturated salt solutions. A bar soap/concentrate composition to be measured is placed in the chamber held at ambient temperature which is then allowed to equilibrate with the headspace in the chamber. At equilibrium, the relative humidity of the air in the chamber is the same as the water activity of the composition.

For purposes of the present invention, the water activity (Aw) of a bar soap composition can be measured using a Hygrolab 3 Water Activity Meter available from Rotronic, Inc. (Huntington, N.Y., USA). The following procedure is employed to determine the water activity (Aw) of a bar soap composition:

1. Check the chamber of the meter to make sure it is clean and dry before the test;
2. Cut a bar soap/concentrate composition into pieces of about 0.2-0.4 cm thick with a stainless steel knife;

3. Put the soap pieces into a clean, dry plastic sample container with a depth of ½";
4. Press the soap pieces with a gloved finger lightly to make sure that the bottom of the container is covered by the soap pieces;
5. Put the sample container back into the chamber of the meter and cover it with the chamber top, which contains the electronic headspace measurement apparatus;
6. Wait for the headspace to reach equilibrium (approximately 1-2 hours); and
7. Record the temperature and the Aw value.

Preferably, but not necessarily, the bar soap/concentrate compositions of the present invention are characterized by a water activity of less than 0.9, more preferably between about 0.4 and 0.9, still more preferably between 0.5 and 0.9, and most preferably between 0.6 and 0.9. The bar soap can be manufactured with a water activity of about 0.85, and during distribution, such bar soap can dehydrate to obtain a lower water activity of between 0.5 and 0.8, or between 0.55 and 0.75, or between 0.6 and 0.75.

Penetration Hardness

The penetration hardness test provides a method to assess the stickiness of the concentrate composition by measuring the force (N) required to break a cake formed by compressing the concentrate particles. The stickier the concentrate particles, the greater the force (N) is required to break the cake. The force (N) required to break the cake is measured at 25° C., 15% relative humidity, using a Force Gauge Machine (Model Z2-44) as depicted in FIG. 2D, and available from IMADA Inc. (Illinois, USA). The following procedure is employed to determine the penetration hardness of the concentrate compositions:

1. Prepare the solid concentrate composition containing ZPT of the present invention according to the method as disclosed herein above. This concentrate composition can be any solid forms such as, for example, powders, granules, pellets, noodles, chunks, bars and the like.
2. Prepare the cake form by compressing the solid concentrate particles prepared in step 1 in a sleeve-confined space, with reference to FIGS. 2A-2C, according to the following steps:

(i) Place a solid perspex cylinder with polished surface with a diameter of 6.35 cm, length of 15.90 cm, and having a hole with a diameter of 0.65 cm through the center of the cylinder and positioned about 9.20 cm from the bottom of the cylinder, as shown in FIG. 2A, under a force gauge machine. Place a perspex sleeve with polished inner surface with the inner diameter of 6.40 cm, length of 15.90 cm, along the outside of the cylinder. Ensure that the cylinder and sleeve are clean and the sleeve moves freely along the cylinder.

(ii) Place a pin (i.e., locking pin) into a hole in the cylinder and rest the sleeve thereon to form a confined space on the top of the cylinder having a volume of 291.2 cm$^3$.

(iii) Grind the concentrate composition into small concentrate particles with particle size smaller than 1 cm.

(iv) Fill the confined space on the top of the cylinder with the concentrate particles as shown in FIG. 2A. With a straightedge, level the concentrate particles with the top of the sleeve.

(v) Place a lid on top of the sleeve, and then carefully place a 5 Kg weight on top of the lid.

(vi) Remove the locking pin as shown in FIG. 2B.

(vii) After 5 mins, remove the 5 Kg weight and slide the sleeve down, as shown in FIG. 2C, to form the concentrate cake.

3. Measure the force (N) required for a probe to break the concentrate cake using the Force Gauge Machine, with reference to FIG. 2D, and record the peak force (N) value.

(i) Set the force gauge to 0 N and turn on the machine. Switch on the motor to direct the gauge downward to the center of the lid.

(ii) Record the peak force (N) required to break the cake, which is equal to the cake strength or the concentrate composition stickiness.

Note. The Force Gauge Machine and the method as described hereinabove are calibrated according to known standards to those skilled in the art and that are commercially available.

EXAMPLES

Example 1—Comparative ZPT Stability Test of Concentrate Compositions

Seven different concentrate compositions (Examples A-G) are prepared containing soap noodles with varying levels of ZPT, uncomplexed HEDP, and talc as listed in Table 2 below.

TABLE 2

| Raw Materials | Amount (w/w %) | | | | | | |
|---|---|---|---|---|---|---|---|
| | Ex. A | Ex. B | Ex. C | Ex. D | Ex. E | Ex. F | Ex. G |
| Dry Soap Noodle* | 35.62 | 19.17 | 40.87 | 60.10 | 20.38 | 48.66 | 37.34 |
| ZPT (48% active) | 15.15 | 22.26 | 18.10 | 15.47 | 18.40 | 12.05 | 16.72 |
| HEDP-4Na | 5.19 | 7.63 | 6.20 | 5.30 | 6.31 | 2.41 | 3.34 |
| ZnSO4•7H2O** | 4.04 | 5.94 | 4.83 | 4.13 | 4.91 | 1.88 | 2.60 |
| Talc | 40.00 | 45.00 | 30.00 | 15.00 | 50.00 | 35.00 | 40.00 |
| Total | 100.00 | 100.00 | 100.00 | 100.00 | 100.00 | 100.00 | 100.00 |
| pH (1% solution) | 10.09 | 9.83 | 10.14 | 10.20 | 9.86 | 10.25 | 10.21 |

*The soap noodle contained the ingredients in Table 3.
**Analytical grade available from Tianjin Jiaxin Chemicals Glass Instrument Trading Co., Ltd.

TABLE 3

| Ingredients | Wt % |
|---|---|
| Sodium palmate (from palm oil and palm oil sterine) | 49.683 |
| Sodium tallowate (from tallow) | 16.027 |
| Sodium palm kernelate (from palm kernel oil) | 14.424 |
| Unsaponifiable matter | 0.540 |
| Citric acid (anhydrous) | 0.100 |
| Sodium citrate | 0.152 |

TABLE 3-continued

| Ingredients | Wt % |
| --- | --- |
| Pentasodium pentetate | 0.050 |
| Tetrasodium etidronate | 0.050 |
| Sodium chloride (low sodium) | 0.553 |
| Glycerine | 3.471 |
| Coconut acid | 0.950 |
| DI Water | Q.S. |

The initial ZPT contents of Examples A-G are measured according to the ZPT stability test procedures described hereinabove. The samples are then subjected to environment stresses in an incubator at 40° C. with 60% relative humidity (RH) for 90 days, after which the final ZPT contents were re-measured and used to calculate the ZPT loss (w/w %). The results are summarized in Table 4.

TABLE 4

| Results | Ex. A | Ex. B | Ex. C | Ex. D | Ex. E | Ex. F | Ex. G |
| --- | --- | --- | --- | --- | --- | --- | --- |
| Initial ZPT Content (w/w %) | 7.272 | 10.684 | 8.686 | 7.426 | 8.834 | 5.785 | 8.026 |
| Final ZPT Content (w/w %) | 7.266 | 10.611 | 8.681 | 7.394 | 8.917 | 5.768 | 7.877 |
| ZPT Loss (w/w %) | 0.006 | 0.073 | 0.005 | 0.032 | (0.083) | 0.017 | 0.149 |

The ZPT loss (w/w %) from the above Examples are plotted in FIG. 1, which demonstrates that there is no significant ZPT loss for concentrate composition at varying ZPT levels.

Example 2—Comparative ZPT Stability Test of Bar Soaps

Two different bar soaps Examples H and I are prepared from the concentrate composition and other listed ingredients in Table 5.

TABLE 5

| | Amount (w/w %) | |
| --- | --- | --- |
| Raw Materials | Example H | Example I |
| Dry Soap Noodle* | 75.97 | 75.67 |
| ZPT concentrate (10%) | 2.40 | 2.40 |
| Starch | 20.00 | 20.00 |
| Perfume | 1.10 | 1.40 |

TABLE 5-continued

| | Amount (w/w %) | |
| --- | --- | --- |
| Raw Materials | Example H | Example I |
| Tinogard TT** | 0.03 | 0.03 |
| Dye | 0.01 | 0.01 |
| DI water | Q.S. | Q.S. |
| pH (1% solution) | 10.26 | 10.19 |

*The soap noodle contained the ingredients in Table 3.
**Commercially available as Tinogard ® TT from BASF (Monheim, Germany).

The initial ZPT contents of Examples H and I are measured according to the ZPT stability test procedures described hereinabove. The samples are then subjected to environment stresses in an incubator at 40° C. with 60% relative humidity (RH) for 90 days, after which the final ZPT contents were re-measured and used to calculate the ZPT loss (w/w %). The results are summarized in Table 6 and demonstrate no significant ZPT loss for bar soaps made from concentrate compositions.

TABLE 6

| Results | Example H | Example I |
| --- | --- | --- |
| Initial ZPT Content (w/w %) | 0.240 | 0.240 |
| Final ZPT Content (w/w %) | 0.224 | 0.221 |
| ZPT Loss (w/w %) | 0.016 | 0.019 |

Example 3—Penetration Hardness Test of the Concentrate Compositions

Seven different concentrate compositions (Examples J-P) are prepared containing soap noodles with varying levels of ZPT and talc as listed in Table 7 below. The moisture was measured by a Karl Fischer Auto Titrator with the following procedures:
1. Cut sample into small pieces and then weigh out 0.200-0.300 g samples with weight paper.
2. Zero the balance.
3. Add the weighted samples to the titrator vessel careful to avoid spillage. Re-seal the vessel and return the weight paper onto the balance.
4. Record the consumed weight (expressed as the difference on the balance).
5. Enter the consumed weight into the Auto Titrator.
6. Press "ok" to confirm the sample weight. Titration will be performed and data will be printed automatically once the experiment completes.

TABLE 7

| | Amount (w/w %) | | | | | | |
| --- | --- | --- | --- | --- | --- | --- | --- |
| Raw Materials | Ex. J | Ex. K | Ex. L | Ex. M | Ex. N | Ex. O | Ex. P |
| Dry Soap Noodle* | 4.00 | 8.60 | 39.60 | 59.60 | 77.10 | 70.40 | 69.60 |
| ZPT (48% active) | 8.00 | 10.40 | 10.40 | 10.40 | 10.40 | 10.40 | 10.40 |
| Talc | 88.00 | 81.00 | 50.00 | 30.00 | 10.00 | 10.00 | 5.00 |
| DI Water | 0.00 | 0.00 | 0.00 | 0.00 | 2.5 | 9.00 | 15.00 |
| Moisture | 3.38% | 5.10% | 8.54% | 10.33% | 14.26% | 19.60% | 27.03% |

*The soap noodle contained the ingredients in Table 3.

The force (N) required to break the cakes (Examples J-P) are measured according to the Penetration Hardness test procedures described hereinabove. The results are summarized below in Table 8.

TABLE 8

| Results | Ex. J | Ex. K | Ex. L | Ex. M | Ex. N | Ex. O | Ex. P |
|---|---|---|---|---|---|---|---|
| Penetration Force (N) | 16.83 | 20.63 | 30.80 | 26.78 | 25.83 | 42.16 | 89.83 |

See FIG. 3A-D, wherein in FIG. 3A depicts concentrate composition with a penetration hardness of <20 N, FIG. 3B depicts concentrate composition with a penetration hardness of ~20 N, FIG. 3C depicts concentrate composition with a penetration hardness of between 20 N to 50 N, and FIG. 3D depicts concentrate composition with a penetration hardness of >50 N. Therefore, it is preferred that the concentrate compositions of the present invention are characterized by a penetration hardness of 20 N to 50 N, to provide for compositions with the right degree of stickiness.

All ratios are weight ratios unless specifically stated otherwise. All temperatures are in Celsius degrees (° C.), unless specifically stated otherwise. All dimensions and values disclosed herein (e.g., quantities, percentages, portions, and proportions) are not to be understood as being strictly limited to the exact numerical values recited. Instead, unless otherwise specified, each such dimension or value is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of forming a bar soap, comprising the steps of:
   a) forming a mixture by diluting a solid concentrate composition with soap, wherein the solid concentrate comprises from 5% to 25% by weight of a zinc pyrithione and from 8% to 85% by weight of at least one surfactant; and
   b) shaping the mixture to form a bar soap;
   wherein the solid concentrate composition has a penetration hardness of between 20 N and 50 N according to the test method as disclosed herein;
   wherein the surfactant comprises soap;
   wherein the concentrate comprises from 6% to 8%, by weight of the concentrate, of the zinc pyrithione;
   wherein the concentrate further comprises from 1.4% to 15% by weight of the concentrate of a chelant, wherein the chelant has a log $K_{ZnL}$ of greater than 2, wherein the log $K_{ZnL}$ is the log of a conditional stability constant of the chelant with Zn calculated at pH 7, 25° C., 0.1 M NaCl; and
   wherein the concentrate further comprises from 1.4% to 15% by weight of the concentrate of a chelant and wherein the chelant is a metal phosphonate complex comprising one or more phosphonate chelants co-ordinately bonded to one or more metal ions.

2. The method according to claim 1, wherein the concentrate further comprises from 1.4% to 15% by weight of the concentrate of a metal-pyridine oxide complex that is co-ordinately bonded to a metal ion.

3. The method according to claim 1, wherein the one or more chelants are selected from the group consisting of 2-aminoethyl phosphoric acid, N-phosphonomethyl aminodiacetic acid, 1-hydroxyethane-1,1-diphosphonic acid, amino tris(methylene phosphonic acid), ethylenediamine tetra(methylene phosphonic acid), diethylenetriamine penta(methylene phosphonic acid), phytic acid, nitrilotrimethylene phosphonic acid, and combinations thereof.

4. The method according to claim 3, wherein the one or more chelants comprise HEDP.

5. A method of forming a bar soap, comprising:
   a) combining a soap with a concentrate composition to form a mixture, wherein the concentrate composition comprises:
      i) from about 5% to about 25%, by weight of the concentrate, of a zinc pyrithione,
      ii) from about 8% to about 85%, by weight of the concentrate, of a second soap,
      iii) a chelant;
      iv) a zinc salt; and
      v) a filler; and
   b) forming the mixture into a bar soap;
   wherein the chelant comprises a metal-pyridine oxide complex or a metal phosphonate complex and where the zinc salt is selected from the group consisting of zinc carbonate, zinc sulfate, zinc nitrate, zinc fluoride, zinc chloride, zinc borate, zinc oxide, and a combination thereof.

6. The method of claim 5, wherein the filler comprises talc.

* * * * *